(12) United States Patent
Demmer et al.

(10) Patent No.: US 8,781,584 B2
(45) Date of Patent: Jul. 15, 2014

(54) CAPTURE THRESHOLD MEASUREMENT FOR SELECTION OF PACING VECTOR

(71) Applicant: Medtronic, Inc., Minneapolis, MN (US)

(72) Inventors: Wade M. Demmer, Coon Rapids, MN (US); Greggory R. Herr, Blaine, MN (US); Supriya Ketkar, Plymouth, MN (US); Karen J. Kleckner, New Brighton, MN (US); Todd J. Sheldon, North Oaks, MN (US); Robert W. Stadler, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/790,683

(22) Filed: Mar. 8, 2013

(65) Prior Publication Data
US 2014/0135867 A1     May 15, 2014

Related U.S. Application Data

(60) Provisional application No. 61/726,760, filed on Nov. 15, 2012.

(51) Int. Cl.
*A61N 1/37* (2006.01)
(52) U.S. Cl.
USPC .......................................................... 607/23
(58) Field of Classification Search
USPC .................................................. 607/28–29
See application file for complete search history.

(56) References Cited

U.S. PATENT DOCUMENTS

| | | | |
|---|---|---|---|
| 6,915,164 B2 | 7/2005 | Bradley | |
| 7,433,736 B2 * | 10/2008 | Rueter et al. | 607/28 |
| 8,271,086 B2 | 9/2012 | Bohn | |
| 2010/0137935 A1 * | 6/2010 | Parikh et al. | 607/28 |
| 2010/0198292 A1 * | 8/2010 | Honeck et al. | 607/17 |
| 2012/0078320 A1 | 3/2012 | Schotzko et al. | |
| 2012/0101543 A1 * | 4/2012 | Demmer et al. | 607/28 |
| 2012/0165895 A1 | 6/2012 | Dong et al. | |

FOREIGN PATENT DOCUMENTS

| | | |
|---|---|---|
| EP | 1620176 A2 | 4/2004 |
| EP | 1542765 A1 | 6/2005 |
| EP | 1694405 A2 | 8/2006 |
| EP | 1291038 B1 | 6/2007 |
| EP | 1833563 A1 | 9/2007 |
| EP | 1896126 A1 | 3/2008 |

OTHER PUBLICATIONS (PCT/US2013/066364) PCT Notification of Transmittal of the International Search Report and the Written Opinion of the International Searching Authority.

* cited by examiner

*Primary Examiner* — Carl H Layno
*Assistant Examiner* — Paula J Stice
(74) *Attorney, Agent, or Firm* — Michael C. Soldner

(57) ABSTRACT

Various techniques for facilitating selection of a pacing vector for pacing a chamber of a heart are described. One example method described includes, for each of a plurality of vectors, delivering a pacing pulse to capture a first heart chamber, determining a first time interval between the pacing pulse and a sensed event in a second heart chamber, determining a capture detection window in response to the determined first time interval, and enabling a capture detection module to iteratively decrease a pacing pulse magnitude delivered in the first heart chamber until an event in the second heart chamber is not sensed during the determined capture detection window.

22 Claims, 8 Drawing Sheets

CAPTURE THRESHOLD MEASUREMENT FOR SELECTION OF PACING VECTOR

RELATED APPLICATION

The present application claims priority and other benefits from U.S. Provisional Patent Application Ser. No. 61/726,760, filed Nov. 15, 2012, entitled "CAPTURE THRESHOLD MEASUREMENT FOR SELECTION OF PACING VECTOR", incorporated herein by reference in its entirety.

TECHNICAL FIELD

This disclosure relates to implantable medical devices, and more particularly, to implantable medical devices that deliver cardiac pacing.

BACKGROUND

A wide variety of implantable medical devices for delivering a therapy or monitoring a physiologic condition have been clinically implanted or proposed for clinical implantation in patients. In some cases, implantable medical devices (IMD) deliver electrical stimulation therapy and/or monitor physiological signals via one or more electrodes or sensor elements, which may be included as part of one or more elongated implantable medical leads. Implantable medical leads may be configured to allow electrodes or sensors to be positioned at desired locations for sensing or delivery of stimulation. For example, electrodes or sensors may be carried at a distal portion of the lead. A proximal portion of the lead that may be coupled to an implantable medical device housing, which may contain electronic circuitry such as stimulation generation and/or sensing circuitry.

For example, implantable medical devices, such as cardiac pacemakers or implantable cardioverter defibrillators, provide therapeutic stimulation to the heart by delivering electrical therapy signals, such as pulses for pacing, or shocks for cardioversion or defibrillation, via electrodes of one or more implantable leads. In some cases, such an implantable medical device may sense for intrinsic depolarizations of the heart, and control the delivery of such signals to the heart based on the sensing. When an abnormal rhythm is detected, which may be bradycardia, tachycardia or fibrillation, an appropriate electrical signal or signals may be delivered to restore the normal rhythm. For example, in some cases, an implantable medical device may deliver pacing, cardioversion or defibrillation signals to the heart of the patient upon detecting ventricular tachycardia, and deliver defibrillation electrical signals to a patient's heart upon detecting ventricular fibrillation. Pacing signals typically have a lower energy than the cardioversion or defibrillation signals.

Patients with heart failure are, in some cases, treated with cardiac resynchronization therapy (CRT). CRT is a form of cardiac pacing. In some examples, CRT involves delivery of pacing pulses to both ventricles to synchronize their contraction. In other examples, CRT involves delivery of pacing pulses to one ventricle to synchronize its contraction with that of the other ventricular, such as pacing the left ventricle to synchronize its contraction with that of the right ventricle. CRT is one example of a variety of modes of cardiac pacing in which stimulation is delivered to one chamber or location at a time that is an interval before or after an event at another chamber or location. The event at the other chamber or location may be the delivery of a pacing pulse to the other chamber or location, or the detection of an intrinsic cardiac depolarization at the other chamber or location.

Various methods exist for detecting whether a pacing stimulus has captured the heart and determining capture thresholds. In some examples, a first pair of electrodes delivers a pacing pulse to a chamber, and the same or a different pair of electrodes detects an electrical signal, e.g., evoked response, in the chamber indicative of capture. In other examples, a device detects a mechanical contraction of the heart at the target site as evidence of capture of the heart by the pacing stimulus. In general, capture threshold determination or management involves delivery of pacing stimuli at incrementally increasing or decreasing magnitudes, e.g., voltage or current amplitudes or pulse widths, and identification of the magnitude at which capture or loss of capture occurs.

DETAILED DESCRIPTION

This disclosure describes techniques for measuring heart tissue pacing capture thresholds for a plurality of vectors to facilitate selection of one of the vectors based on the capture thresholds. The time interval between delivery of a pacing stimulus to a first chamber of the heart and a subsequent depolarization of a second chamber of the heart may be useful in determining whether capture of the first chamber has occurred following the delivered pacing stimulus. For example, using various techniques of this disclosure, the time interval between a left ventricle (LV) pace and a right ventricle (RV) depolarization or sense (where no pacing pulse is delivered to the RV) may be used to determine whether the pacing stimulus captured the LV. Delivery of a pacing stimulus to the LV during a cardiac cycle without also delivering a pacing stimulus to the RV may be referred to as an LV-only pace or LV-only pacing.

Then, the LV pace (LVP) to RV sense (RVS) interval may be used to discriminate between capture and loss-of-capture (LOC). If the pacing pulse captured, then the magnitude, e.g., voltage amplitude, of the pacing pulse may be decreased until LOC is detected. If the pacing pulse did not capture, then the magnitude may be increased until capture occurs, then decremented until LOC occurs. In this manner, the techniques of this disclosure may quickly and accurately measure the estimated tissue pacing capture thresholds for one or more pacing vector configurations, thereby allowing a clinician to select particular vectors for the implantable medical device (IMD) that will deliver sufficient energy to pace the heart without unnecessarily depleting the battery.

Although the following description refers to examples in which a pacing pulse is delivered to the LV and depolarizations are sensed in the RV to determine an LVP-RVS interval, and whether the LVP captured the LV based on the LVP-RVS interval, it is to be understood that the disclosure is broadly applicable to any chambers of the heart being the stimulated chamber or sensing chamber, and to any type of stimulation. Furthermore, although described herein primarily with reference to examples in which voltage amplitude is adjusted during the test for a vector to identify a voltage amplitude at which capture/LOC occurs, the techniques are applicable to examples in which any one or more parameters that effects the magnitude of the pacing stimulus are adjusted.

Figure 1:
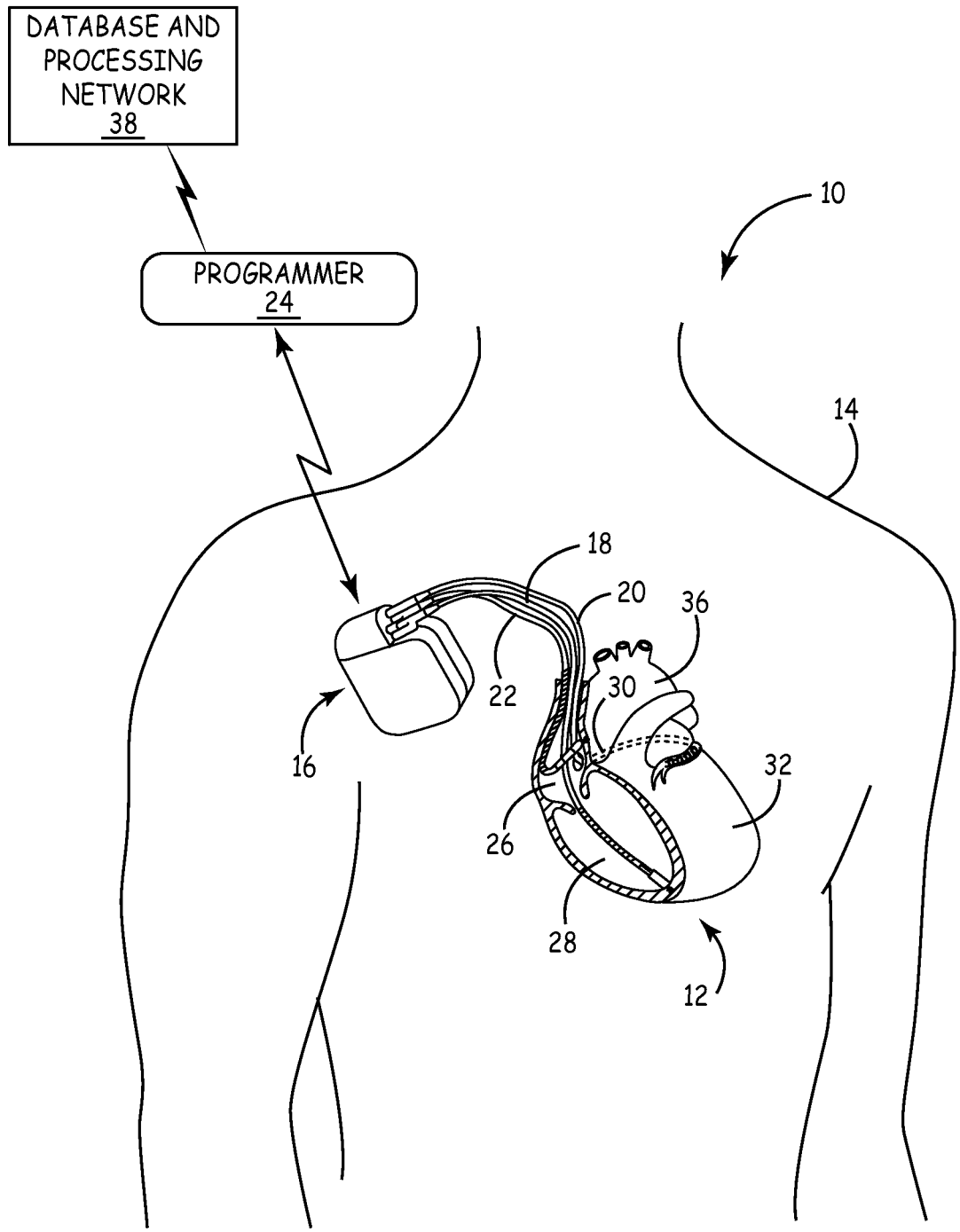
FIG. 1 is a conceptual diagram illustrating an example system that may be used to provide therapy to and/or monitor a heart of a patient.

FIG. 1 is a conceptual diagram illustrating an example system 10 that may be used to monitor and/or provide therapy to heart 12 of patient 14. Patient 14 ordinarily, but not necessarily, will be a human. System 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. In accordance with this disclosure, IMD 16 may deliver LV-only pacing pulses via a plurality of pacing vectors that include at least one electrode on lead 20 in order to assess LVP-RVS intervals to discriminate between capture and LOC, as will be described in greater detail below.

Leads 18, 20, 22 extend into the heart 12 of patient 16 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 detects fibrillation employing one or more fibrillation detection techniques known in the art.

Using various techniques of this disclosure, IMD 16 may deliver LV-only pacing pulses via various combinations of electrodes that include at least one electrode on LV coronary sinus lead 20, for example. Subsequent to the delivery of each of the LV-only pacing pulses, electrical activity of the RV may be sensed by another combination of electrodes that includes at least one electrode on RV lead 18. If a depolarization of the right ventricular is sensed (RVS), the LVP-RVS interval may be determined. The intervals between the LVP and a RVS may be used to determine whether the LVP captured the LV. If the pacing pulse captured, then the amplitude of the voltage of the pacing pulse delivered via LV coronary sinus lead 20 may be decreased until LOC is detected. If the pacing pulse did not capture, then the amplitude of the pacing pulse may be increased until capture occurs, or decremented from a higher voltage value until LOC occurs.

IMD 16 may provide the measured intervals, data derived therefrom or alerts based thereon to programmer 24 via wireless telemetry. In some examples, programmer 24 may be a handheld computing device or a computer workstation. A user, such as a physician, technician, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20 and 22, or a power source of IMD 16. The user may use programmer 24 to program a therapy progression, select electrodes used to deliver defibrillation pulses, select waveforms for the defibrillation pulse, or select or configure a fibrillation detection algorithm for IMD 16. The user may also use programmer 24 to program aspects of other therapies provided by IMD 14, such as cardioversion or pacing therapies including CRT.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Programmer 24 may include a processor, memory, user interface, telemetry module, and power source. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with programmer 24 via a user interface, which may include a display to present graphical user interface to a user, and a keypad or another mechanism for receiving input from a user. The user, e.g., a clinician, may define or select vectors to be tested and/or input vector impedance values via the user interface.

Programmer 24 may display pacing vectors to be tested for determining and comparing capture thresholds as well as the results of the pacing capture threshold tests performed using techniques described herein to the clinician. Each vector tested may be displayed with an associated pacing capture threshold pulse energy magnitude, in some order that the clinician may select or adjust. In some example, an impedance of each tested vector may also be displayed. The results of the tests may also be stored within programmer memory.

As indicated above, programmer 24 may communicate wirelessly with IMD 16, such as using RF communication or proximal inductive interaction. This wireless communication is possible through the use of a telemetry module, which may be coupled to an internal antenna or an external antenna.

Programmer 24 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a database and processing network 38 capable of receiving and processing information retrieved from IMD 16.

Database and processing network 38 may include a server, and one or more computing devices that are coupled to the IMD 16 and programmer 24 via a network communication system. In this example, IMD 16 may use its telemetry module to communicate with programmer 24 via a first wireless connection, and to communicate with database and processing network 38 via a second wireless connection. Database and processing network 38 may include one or more processors, such as one or more microprocessors, DSPs, ASICs, FPGAs, programmable logic circuitry, or the like, that may perform various functions and operations, such as those described herein. Database and processing network 38 9 may be implemented, in some aspects, with general network technology and functionality similar to that provided by the Medtronic CARELINK® Network developed by Medtronic, Inc., of Minneapolis, Minn.

In some examples, programmer 24 and/or one or more processors of one or more networked computers of network 38 may perform all or a portion of the techniques described herein with respect to processing functions performed by IMD 16. For example, programmer 24 or another processor coupled to IMD system 10 may receive voltages or currents measured by IMD 16 to calculate impedance measurements, or may receive impedance measurements from IMD 16. Programmer 24 or another processor may determine LVP-RVS conduction times using any of the techniques described in this disclosure.

Figure 2:
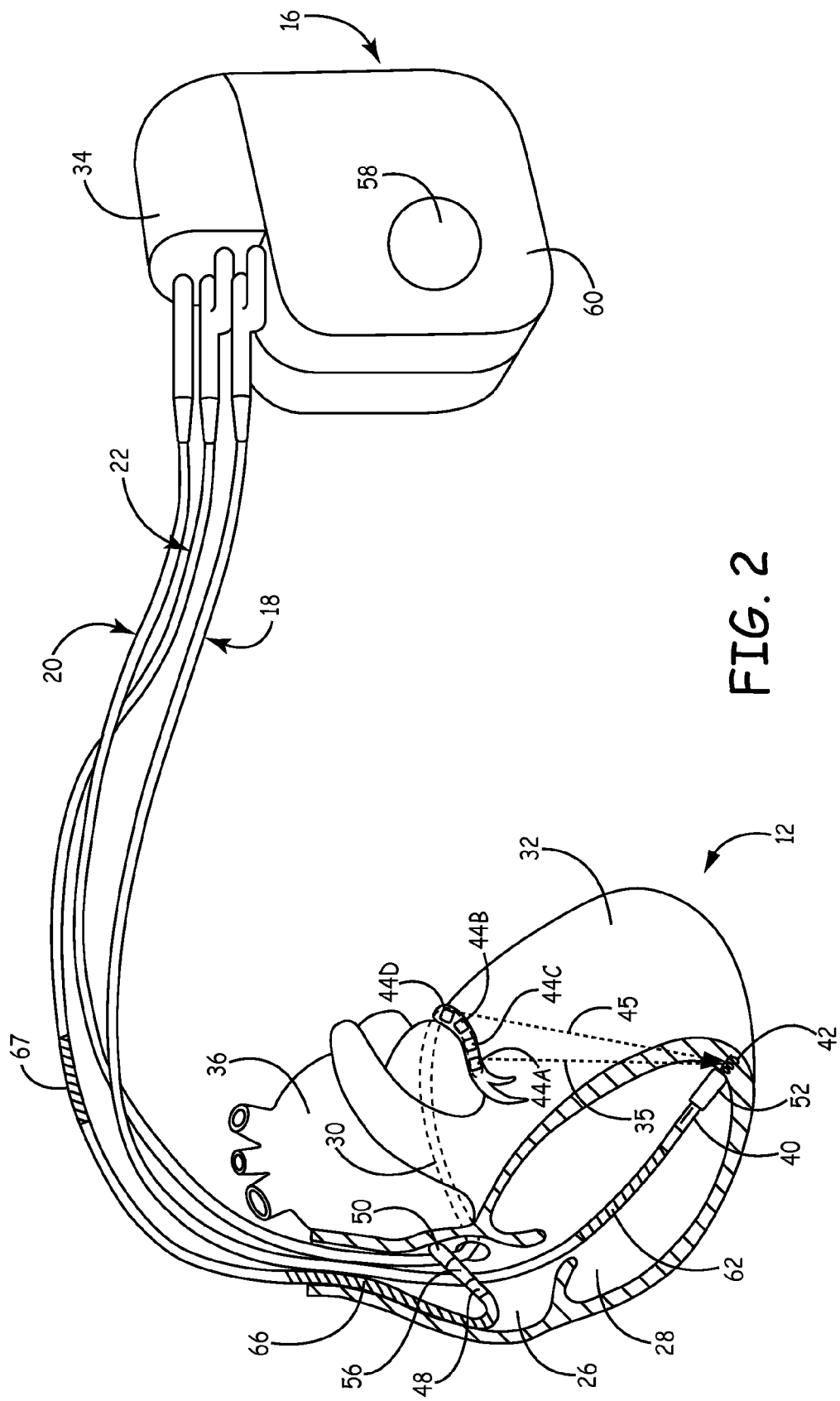
FIG. 2 is a conceptual diagram illustrating the example implantable medical device (IMD) and the leads of the system shown in FIG. 1 in greater detail.

FIG. 2 is a conceptual diagram illustrating IMD 16 and leads 18, 20, and 22 of therapy system 10 in greater detail. Leads 18, 20, 22 may be electrically coupled to a signal generator and a sensing module of IMD 16 via connector block 34. Each of the leads 18, 20, 22 includes an elongated insulative lead body carrying one or more conductors. Bipolar electrodes 40 and 42 are located adjacent to a distal end of lead 18 and bipolar electrodes 48 and 50 are located adjacent to a distal end of lead 22. In some example configurations, lead 20 may be a quadripolar lead and, as such, include four electrodes, namely electrodes 44A-44D, which are located adjacent to a distal end of lead 20. Electrodes 40, 44A-44D, and 48 may take the form of ring electrodes, and electrodes 42 and 50 may take the form of extendable helix tip electrodes mounted retractably within insulative electrode heads 52 and 56, respectively.

Leads 18 and 22 also include elongated intracardiac electrodes 62 and 66 respectively, which may take the form of a coil. In addition, one of leads 18, 20, 22, e.g., lead 22 as seen in FIG. 2, may include a superior vena cava (SVC) coil 67 for delivery of electrical stimulation, e.g., transvenous defibrillation. For example, lead 22 may be inserted through the superior vena cava and SVC coil 67 may be placed, for example, at the right atrial/SVC junction (low SVC) or in the left subclavian vein (high SVC). Each of the electrodes 40, 42, 44A-44D, 48, 50, 62, 66 and 67 may be electrically coupled to a respective one of the conductors within the lead body of its associated lead 18, 20, 22, and thereby individually coupled to the signal generator and sensing module of IMD 16.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60.

IMD 16 may sense electrical signals attendant to the depolarization and repolarization of heart 12 via electrodes 40, 42, 44A-44D, 48, 50, 58, 62, 66 and 67. The electrical signals are conducted to IMD 16 via the respective leads 18, 20, 22, or in the case of housing electrode 58, a conductor coupled to the housing electrode. IMD 16. Electrical signals may be sensed via any bipolar combination of electrodes 40, 42, 44A-44D, 48, 50, 58, 62, 66 and 67. Furthermore, any of the electrodes 40, 42, 44A-44D, 48, 50, 58, 62, 66 and 67 may be used for unipolar sensing in combination with housing electrode 58.

In some examples, IMD 16 delivers pacing pulses via bipolar combinations of electrodes 40, 42, 44A-44D, 48 and 50 to produce depolarization of cardiac tissue of heart 12. In some examples, IMD 16 delivers pacing pulses via any of electrodes 40, 42, 44A-44D, 48 and 50 in combination with housing electrode 58 in a unipolar configuration. For example, electrodes 40, 42, and/or 58 may be used to deliver RV pacing to heart 12. Additionally or alternatively, electrodes 44A-44D and/or 58 may be used to deliver LV pacing to heart 12, and electrodes 48, 50 and/or 58 may be used to deliver RA pacing to heart 12.

Furthermore, IMD 16 may deliver defibrillation pulses to heart 12 via any combination of elongated electrodes 62, 66 and 67, and housing electrode 58. Electrodes 58, 62, and 66 may also be used to deliver cardioversion pulses to heart 12. Electrodes 62, 66 and 67 may be fabricated from any suitable electrically conductive material, such as, but not limited to, platinum, platinum alloy or other materials known to be usable in implantable defibrillation electrodes.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIGS. 1 and 2. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

In addition, in other examples, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 36.

Two or more electrodes, and the polarity of the electrodes, define a vector, or path, for delivering pacing pulses to heart 12. As described above, there are numerous vectors that may be used to deliver pacing pulses to heart 12. For example, various combinations of the electrodes on a single quadripolar lead, i.e., a lead with four electrodes on the lead, such as lead 20, as well as combinations of the lead electrodes with an electrode on the housing of an IMD may provide sixteen different vectors that may be used to deliver pacing pulses to a chamber of heart 12 that the lead is within or on. Testing each vector in order to determine which vector at a particular voltage amplitude sufficiently captures the heart without unnecessarily depleting the battery, e.g., by pacing at too high a voltage, may be a time-consuming process.

Using the techniques of this disclosure, a clinician may quickly determine one or more electrode combinations of one or more leads of an implantable medical device that have an acceptable, e.g., relatively low, pacing threshold. As described in more detail below, in some cases, the pacing capture techniques may include measuring an interventricular (VV) interval of a patient and, for each of a plurality of vectors, delivering a pacing pulse at a voltage to a left ventricle of a heart, determining whether capture of the left ventricle occurred as a result of the pacing pulse, and iteratively adjusting the voltage and delivering pacing pulses at the adjusted voltages in order to determine a particular voltage at which capture or loss of capture (LOC) of the left ventricle occurs.

Typically capture of the myocardial cells will occur at the cathode electrode of the pacing vector. In some cases, however, a pacing vector may be selected that results in anodal capture or a combination of both anodal and cathodal capture and the presence of anodal and cathodal capture may vary as the pacing pulse energy is varied. In these situations, two different LVP-RVS intervals may exist for a given pacing vector, one LVP-RVS interval corresponding to cathodal capture and another LVP-RVS corresponding to the anodal capture.

This condition is illustrated in FIG. 2. If electrodes 44A and 44D are selected as a bipolar pacing pair, with electrode 44A selected as the cathode and electrode 44D selected as the anode, capture is expected to occur at electrode 44A. An LVP-RVS interval, where the RVS event is sensed at RV tip electrode 42 in this example, may be represented by arrow 35. If, however, anodal capture occurs at electrode 44D, a second LVP-RVS interval represented by arrow 45 will exist for the pacing vector. This second LVP-RVS interval 45 may be longer or shorter than the first LVP-RVS interval 35, which may be related to the physical location of electrode 44D with respect to electrode 44A and tip electrode 42. The pacing capture threshold measurement techniques described herein account for the possibility of having capture at both electrodes of a given electrode vector by automatically adjusting a pacing interval and/or a capture detection window to enable two LVP-RVS intervals of different lengths to be identified for a given electrode vector.

Figure 3:
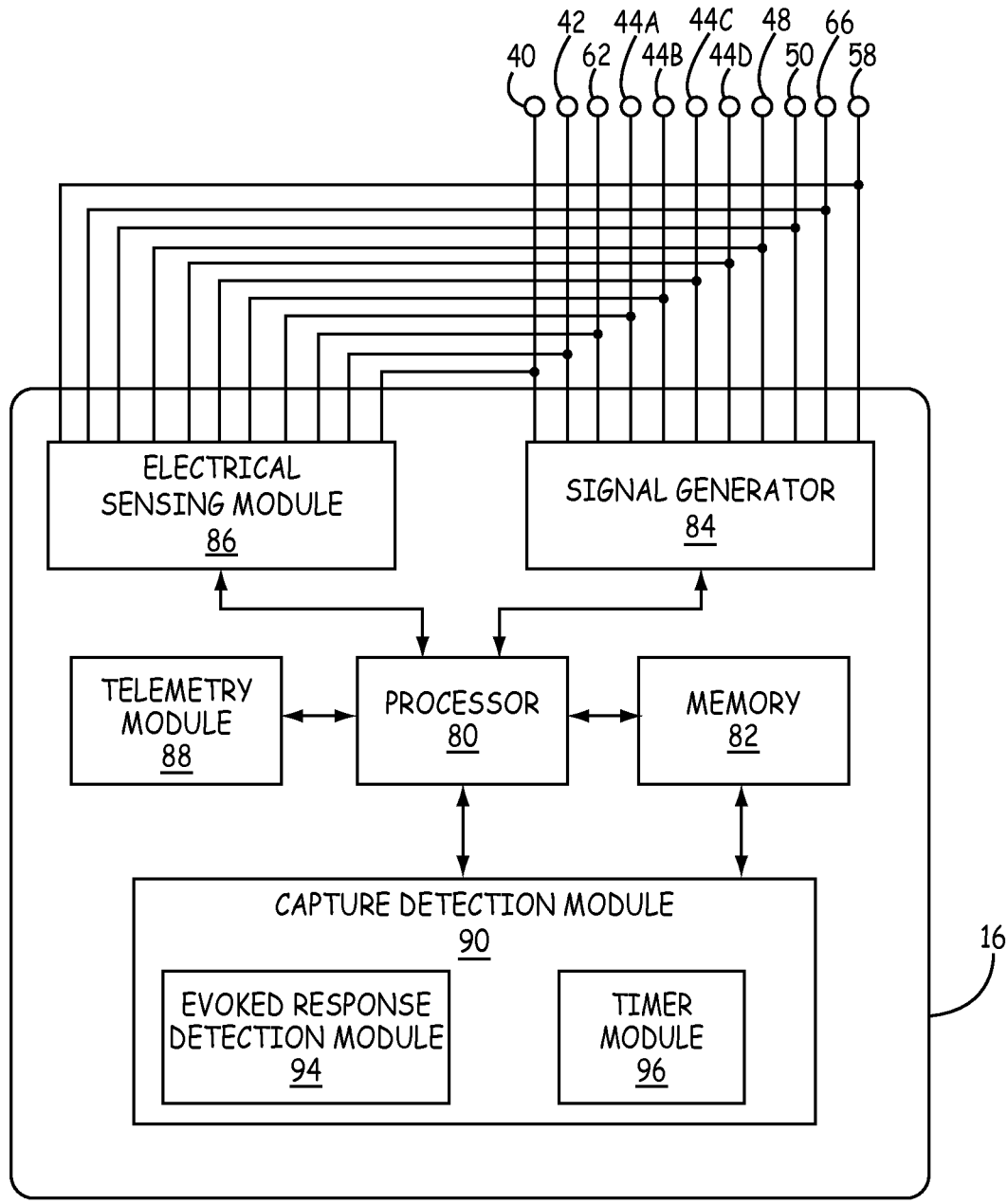
FIG. 3 is a block diagram illustrating an example configuration of an implantable medical device.

FIG. 3 is a block diagram illustrating one example configuration of IMD 16. In the example illustrated by FIG. 3, IMD 16 includes a processor 80, memory 82, signal generator 84, electrical sensing module 86, and telemetry module 88. IMD 16 further includes capture detection module 90, which itself includes evoked response detection module 94 and timer module 96. Memory 82 may include computer-readable instructions that, when executed by processor 80, cause IMD 16 and processor 80 to perform various functions attributed throughout this disclosure to IMD 16, processor 80, or capture detection module 90. The computer-readable instructions may be encoded within memory 82. Memory 82 may comprise computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. In one example, capture detection module 90, evoked response detection module 94, and timer module 96 may be stored or encoded as instructions in memory 82 that are executed by processor 80.

Processor 80 controls signal generator 84 to deliver stimulation therapy, e.g., cardiac pacing or CRT, to heart 12 according to a selected one or more therapy programs, which may be stored in memory 82. Signal generator 84 is electrically coupled to electrodes 40, 42, 44A-44D, 48, 50, 58, 62, and 66, e.g., via conductors of the respective lead 18, 20, 22, or, in the case of housing electrode 58, via an electrical conductor disposed within housing 60 of IMD 16. Signal generator 84 is configured to generate and deliver electrical stimulation therapy to heart 12 via selected combinations of electrodes 40, 42, 44A-44D, 48, 50, 58, 62, and 66. In some examples, signal generator 84 is configured to deliver cardiac pacing pulses. In other examples, signal generator 84 may deliver pacing or other types of stimulation in the form of other signals, such as sine waves, square waves, or other substantially continuous time signals.

Stimulation generator 84 may include a switch module (not shown) and processor 80 may use the switch module to select, e.g., via a data/address bus, which of the available electrodes are used to deliver pacing pulses. Processor 80 may also control which of electrodes 40, 42, 44A-44D, 48, 50, 58, 62, and 66 is coupled to signal generator 84 for generating stimulus pulses, e.g., via the switch module. The switch module may include a switch array, switch matrix, multiplexer, or any other type of switching device suitable to selectively couple a signal to selected electrodes.

Electrical sensing module 86 monitors signals from at least one of electrodes 40, 42, 44A-44D, 48, 50, 58, 62, or 66 in order to monitor electrical activity of heart 12. Electrical sensing module 86 may also include a switch module to select which of the available electrodes are used to sense the cardiac activity. In some examples, processor 80 selects the electrodes that function as sense electrodes, or the sensing vector, via the switch module within electrical sensing module 86.

Electrical sensing module 86 includes multiple detection channels, each of which may be selectively coupled to respective combinations of electrodes 40, 42, 44A-44D, 48, 50, 58, 62, or 66 to detect electrical activity of a particular chamber of heart 12. Each detection channel may comprise an amplifier that outputs an indication to processor 80 in response to detection of an event, such as a depolarization, in the respective chamber of heart 12. In this manner, processor 80 may detect the occurrence of R-waves and P-waves in the various chambers of heart 12.

Memory 82 stores intervals, counters, or other data used by processor 80 to control the delivery of pacing pulses by signal generator 84. Such data may include intervals and counters used by processor 80 to control the delivery pacing pulses to one or both of the left and right ventricles for CRT. The intervals and/or counters are, in some examples, used by processor 80 to control the timing of delivery of pacing pulses relative to an intrinsic or paced event, e.g., in another chamber.

In one example, capture detection module 90 uses signals from electrical sensing module 86 to detect capture and/or inadequate capture when signal generator 84 delivers a pacing pulse. Via the switching module, processor 80 may control which of electrodes 40, 42, 44A-44D, 48, 50, 58, 62, and 66 is coupled to electrical sensing module 86 to detect a depolarization in a second chamber, e.g., the RV, subsequent to the delivery of a pacing pulse to a first chamber, e.g., the LV, for the determination of whether the pacing pulse captured the first chamber. Processor 80 may also control which of electrodes 40, 42, 44A-44D, 48, 50, 58, 62, and 66 is coupled to electrical sensing module 86 to detect an evoked electrical response in the first chamber to the pacing pulse in the first chamber. Memory 82 may store predetermined intervals or voltage thresholds which define whether a detected signal has an adequate magnitude and is appropriately timed relative to the pacing pulse to be considered a depolarization in the second chamber indicative of capture or an evoked response in the first chamber. In some examples, a channel of electrical sensing module 86 used to detect capture comprises an amplifier which provides an indication to processor 80 when a detected signal has an adequate magnitude.

Processor 80 controls the selection of electrode configurations for delivering pacing pulses and for detecting capture and/or loss of capture. Processor 80, for example, may communicate with signal generator 84 to select two or more stimulation electrodes in order to generate one or more pacing pulses for delivery to a selected chamber of heart 12. Processor 80 may also communicate with electrical sensing module 86 to select two or more sensing electrodes for capture detection based on the chamber to which the pacing pulse is delivered by signal generator 84.

Capture detection module 90, in the example of FIG. 3, is capable of detecting capture and LOC during capture detection tests. Capture detection module 90 uses timer module 96 to determine when to deliver pacing pulses and to determine conduction times between chambers of the heart. In addition, as seen in FIG. 3, capture detection module 90 further includes evoked response detection module 94 for detecting the amplitude and timing of an evoked response.

Using certain techniques of this disclosure, capture detection module 90 may determine pacing capture thresholds for each of a plurality of pacing vectors by, for each of the vectors, delivering pacing pulses at various voltage levels, determining left ventricle pace (LVP) to right ventricle sense (RVS) conduction time intervals in response to each of the pacing pulses, and determining a voltage at which capture/loss-of-capture (LOC) occurs.

Briefly, the pacing capture test techniques of this disclosure may include pacing an atrium, measuring an intrinsic atrioventricular (AV) interval of a patient in response to the delivered pace, delivering a pacing pulse at a voltage to the left ventricle of the heart, determining whether capture occurred as a result of the pacing pulse, and iteratively adjusting the voltage and delivering pacing pulses at the adjusted voltages in order to determine a particular voltage at which capture or LOC occurs. In an alternative embodiment, the pacing capture test techniques of this disclosure may include measuring a ventricular rate, overdrive pacing in the LV, determining whether capture occurred as a result of the pacing pulse by sensing an RV event in a capture detection window, and iteratively adjusting the voltage and delivering pacing pulses at the adjusted voltages in order to determine a particular voltage at which capture or LOC occurs in the LV.

Before delivering any pacing pulses for performing a capture threshold test, a basic stability test can be performed on a patient. The basic stability test monitors the patient's current heart rhythm in order to verify the stability and rate of the patient's heart. For example, the stability test may monitor the intrinsic ventricular rate of the patient's heart. If the rate is too high or the heart is unstable, the pacing capture test aborts. If the rate and stability are considered acceptable, however, then the pacing capture test may continue. The amplitude of the pacing pulse, the pacing configuration, and the vector may be recorded and used later as a "normal" configuration for any backup pacing cycles delivered throughout the pacing capture test. A pacing configuration may include programmable pacing settings, such as whether pacing is set to be RV only, RV to LV, LV to RV, or LV only, as well as the rate, amplitude, and other settings that may be altered for the "test" pulses.

The pacing capture threshold test of this disclosure delivers pacing pulses within a range of pacing pulse energy magnitudes, which may be adjusted by varying pacing pulse voltage amplitude, e.g., between about 6V to about 0V. In one example implementation, capture detection module 90 selects an initial voltage to be delivered to the left ventricle of the patient's heart that is approximately in the middle of the range of voltages, e.g., about 3V. The pacing pulse energy magnitude, however, may be adjusted between a range of voltages, pulse widths, or other control parameter that varies the delivered pulse energy.

After the pacing pulse is delivered, electrical sensing module 86 and capture detection module 90 determine whether there is evidence of capture. In accordance with certain techniques of this disclosure, the capture detection module 90 establishes a capture detection window based on an LVP-RVS interval measured when an LVP pulse is delivered with adequate energy to capture the LV. The pacing pulse energy is then iteratively decreased, and electrical sensing module 86 and capture detection module 90 determine if an RVS occurs during the capture detection window. If the RVS occurs during the capture detection window, the LVP has captured the LV.

Figure 4:
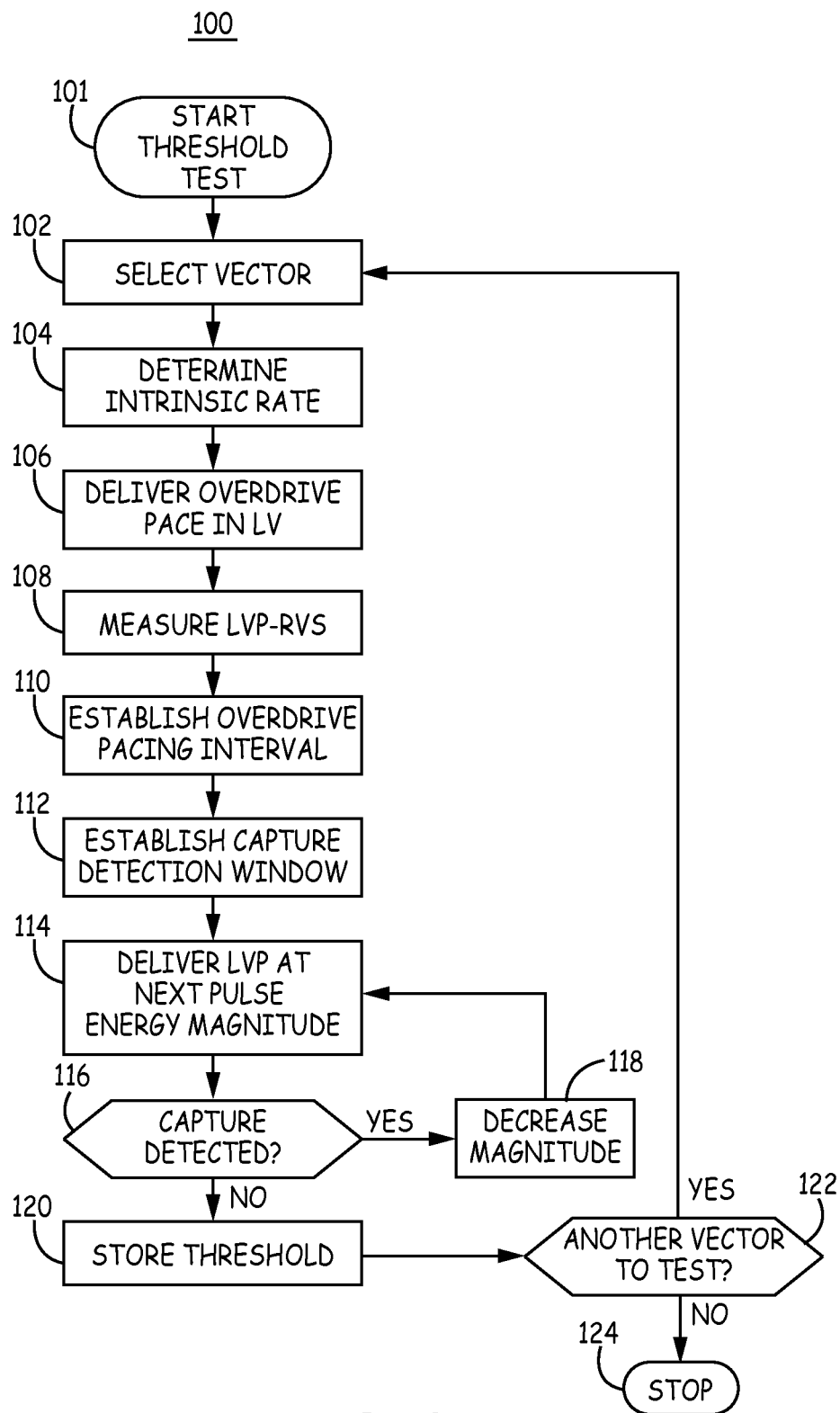
FIG. 4 is a flow chart of a method for performing a capture threshold test according to one embodiment.

FIG. 4 is a flow chart of a method 100 for performing a capture threshold test according to one embodiment. At block 101, a capture threshold test is started by capture detection module 90. The capture threshold test may be initiated by user interacting with programmer 24. At other times, a capture threshold test may be initiated automatically by IMD 16.

At block 102, a pacing vector is selected. The pacing vector includes at least one electrode positioned along the heart chamber for which a capture threshold is being determined. In the illustrative embodiment, a LV capture threshold test is being performed to determine the capture threshold of up to all sixteen possible pacing vectors (twelve bipolar and four unipolar vectors) available using electrodes 44A through 44D.

An intrinsic cardiac rate is determined at block 104 to enable a pacing pulse to be delivered at a rate faster than the intrinsic rate to facilitate determination of capture or LOC of the pacing pulse. For example, the intrinsic ventricular rate is determined at block 104. Determining an intrinsic rate may include determining if the intrinsic rate is stable before proceeding in testing capture, for example, as generally disclosed in U.S. Publication No. 2012/0101543A1 (Demmer, et al.), hereby incorporated herein by reference in its entirety.

The heart chamber in which the capture test is being performed is paced at an interval shorter than the intrinsic rate at block 106 to enable an evoked response in the paced chamber to conduct to a second heart chamber and cause depolarization of the second heart chamber earlier than an expected intrinsic depolarization of the second heart chamber. In the example of the LV capture test, the LV is paced using the selected vector and a pacing pulse amplitude expected to capture the LV with a high probability at an interval shorter than the intrinsic ventricular rate interval. In this way, the ventricles are overdrive paced such that the evoked response to the LV pacing pulse will be conducted to and cause depolarization of the RV earlier than an expected intrinsic RV depolarization conducted from the atria.

Figure 5A:
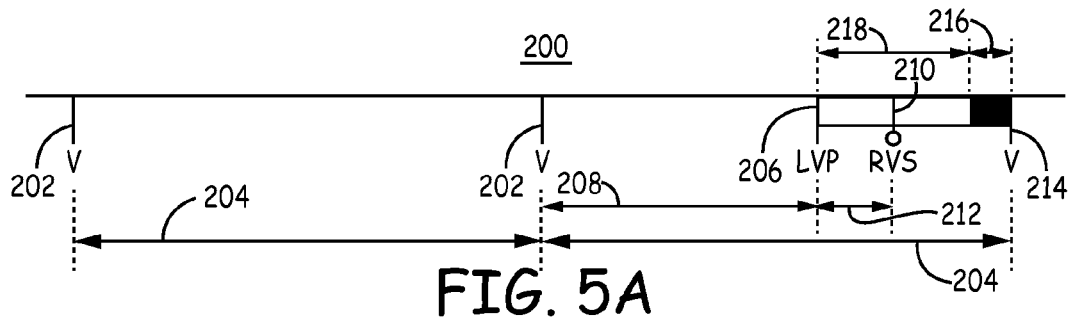
FIG. 5A is a timeline depicting overdrive pacing of the LV.

FIG. 5A is a timeline 200 depicting overdrive pacing of the LV. An intrinsic ventricular rate is measured by measuring a time interval 204 between two sensed ventricular events 202. In this example, the ventricular rate corresponds to an interval of 1000 ms. An LV pacing pulse (LVP) 206 is delivered at a pacing interval 208 that is shorter than the intrinsic ventricular rate interval 204.

The ventricular rate interval 204 defines an interval at which the next expected intrinsic ventricular event 214 would occur if the LVP 206 does not capture the LV. In other words, if no LVP is delivered or if a delivered LVP does not capture the LV, the next expected ventricular depolarization 214 is expected to be sensed at or near the end of the intrinsic ventricular rate interval 204. An expected intrinsic ventricular event interval 216 may be defined as an interval having a predetermined length, e.g. approximately 30 ms, and ending at or near the next expected intrinsic event 214. This expected intrinsic event interval 216 defines a time window in which the intrinsic event is expected if LOC occurs and allows for some variability in the timing of the intrinsic event that can occur even during a stable heart rate. A sensed event occurring within the expected intrinsic event interval 216 is likely to be an intrinsic ventricular event, e.g. conducted from the atria, rather than a conducted depolarization arising from the LVP evoked response.

If the LVP captures the LV, however, and is early enough before the time of the next expected intrinsic depolarization 214, an event (RVS) 210 will be sensed in the RV during the time interval 218 between the LVP and before the expected intrinsic event interval 216. This RVS 210 occurs at an LVP-RVS interval 212, which corresponds to the time required for a pacing-evoked response to be conducted from the capturing LV electrode to the sensing electrode in the RV.

Referring again to FIG. 4, the LVP-RVS interval 212 is measured at block 108 after delivering an overdrive pacing pulse in the LV at block 106 at a pace interval and pulse magnitude expected to capture the LV such that an RVS will occur before the expected intrinsic event interval 216. To promote a high probability of capturing the LV, an LVP may be delivered at a predetermined interval or percentage shorter than the intrinsic ventricular rate and at a relatively high pulse magnitude. The measured LVP-RVS interval 212 is used to adjust the LV overdrive pacing interval at block 110.

Overdrive pacing of the LV facilitates capture threshold determination by measuring a response in the RV. Overdrive pacing of the ventricles at a fast rate for an extended period of time, however, is generally undesirable. Therefore, the process shown by flow chart 100 is intended to minimize the overdrive pacing rate and the number of overdrive pacing intervals required to determine pacing capture thresholds while providing a reliable method for measuring the capture threshold.

Figure 5B:
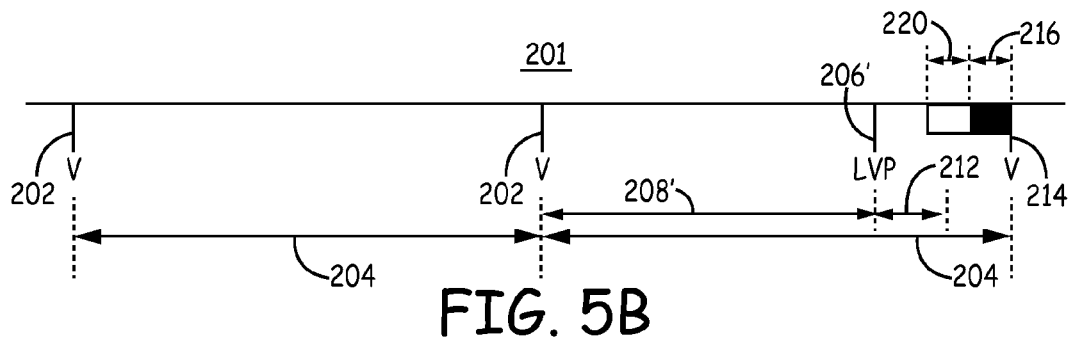
FIG. 5B is a timeline depicting a capture detection window established as a predetermined interval of time extending to the onset of the expected intrinsic event interval.

With reference to the timeline 201 shown in FIG. 5B, a capture detection window 220 is established as a predetermined interval of time ending at or near the onset of the expected intrinsic event interval 216. In one example, the expected intrinsic event interval 216 may be set to be approximately 30 ms. The capture detection window 220 may be set to be approximately 30 ms ending at the onset of the expected intrinsic event interval 216. As used herein, the term "approximately" refers to a range of ±10% of a stated value in some embodiments, and may correspond to a design specification tolerance.

The overdrive LVP interval 208' is set such that the LVP pulse 206' will occur approximately the LVP-RVS interval 212 earlier than a mid-point of the capture detection window 220. Accordingly, an overdrive LVP interval 208' may be computed as the ventricular event rate interval 204 less the expected intrinsic event interval 216, less one-half the capture detection window 220, less the LVP-RVS interval 212 in one example. Other methods may be used to establish an adjusted overdrive LVP interval 208' that is longer than a test interval 208 used to determine the LVP-RVS interval 212 but still enables a capture detection window 220 having a predetermined duration to expires prior to an expected intrinsic event interval 216.

The established LVP interval 208' minimizes the aggressiveness of the overdrive pacing rate while enabling a capture detection window 220 distinctly outside an expected intrinsic event interval 216 to reliably discriminate between evidence of LVP capture and LOC. An RV sensed event occurring during the capture detection window 220 is evidence that LVP 206' captured the LV. An RV sensed event occurring during the expected intrinsic event interval 216 is evidence that the LVP 206' did not capture the LV and can be used to verify LOC. An RVS sensed after LVP 206' and before expected intrinsic event interval 216 but outside capture detection window 220 may be a premature ventricular contraction (PVC). Accordingly, an RVS after LVP 206' but outside windows 216 and 220 is not evidence of LV capture.

In the process shown in FIG. 4, the overdrive pacing interval is established at block 110, e.g. as shown in FIG. 5B, to be the least aggressive pacing interval that allows a capture detection window to be set at block 112 that is reliably distinct from, i.e. expires at or earlier than an onset of, an expected intrinsic event interval. A LVP is delivered at the established overdrive pacing interval at block 114.

An initial pulse energy is set when the first LVP is delivered at block 114. Initially, the LVP may be delivered at a pulse energy magnitude that is in the middle of a range of pulse settings, such as a pulse voltage amplitude setting that is midway between a minimum and maximum amplitude. The pulse energy magnitude may be increased from an initial setting as needed to establish capture at block 114 if the initial setting does not result in capture. For example, the pulse energy magnitude may be set to an initial setting that is midway in a range of settings and if capture is not detected the initial setting is adjusted to or near the maximum setting to establish capture at the adjusted initial setting before proceeding in the process of iteratively decreasing the pulse energy until capture is lost at blocks 116 and 118 as described below. Alternatively, the pulse energy magnitude may initially be set at or near a high end of an available range of settings at block 114.

After delivering an LVP at an initial pulse energy magnitude that does capture the LV, the capture detection module determines whether an RVS occurs during the capture detection window during progressively decreasing pulse energy magnitudes. If an RVS is sensed during the established capture detection window, capture is detected at block 116. A single LV overdrive pacing pulse is delivered to detect capture at the given pulse energy magnitude.

The pacing pulse magnitude is decreased at block 118 in response to capture detection. Another LVP is delivered at the established overdrive pacing interval but at the decreased magnitude at block 114. This process continues until an RVS is no longer sensed during the capture detection window. In some embodiments, this would complete the capture detection test for the selected pacing vector. The capture threshold is stored at block 120 as the last pacing pulse magnitude that resulted in capture detection. If other pacing vectors remain to be tested, as determined at block 122, the next vector is selected at block 102 and the process is repeated. If no other vectors are available to be tested, the capture threshold test is complete and is terminated at block 124.

The process shown in FIG. 4 may be performed, for example, when a unipolar pacing vector is being tested. When a bipolar pacing vector is being tested, however, it is possible to have both anodal capture and cathodal capture occurring for a given bipolar pacing vector. In some cases, anodal capture may be occurring and be lost at a pulse magnitude that may still be high enough to result in cathodal capture (or vice versa). Accordingly, additional steps may be taken to verify that complete LOC has occurred for a test pacing vector.

Figure 6:
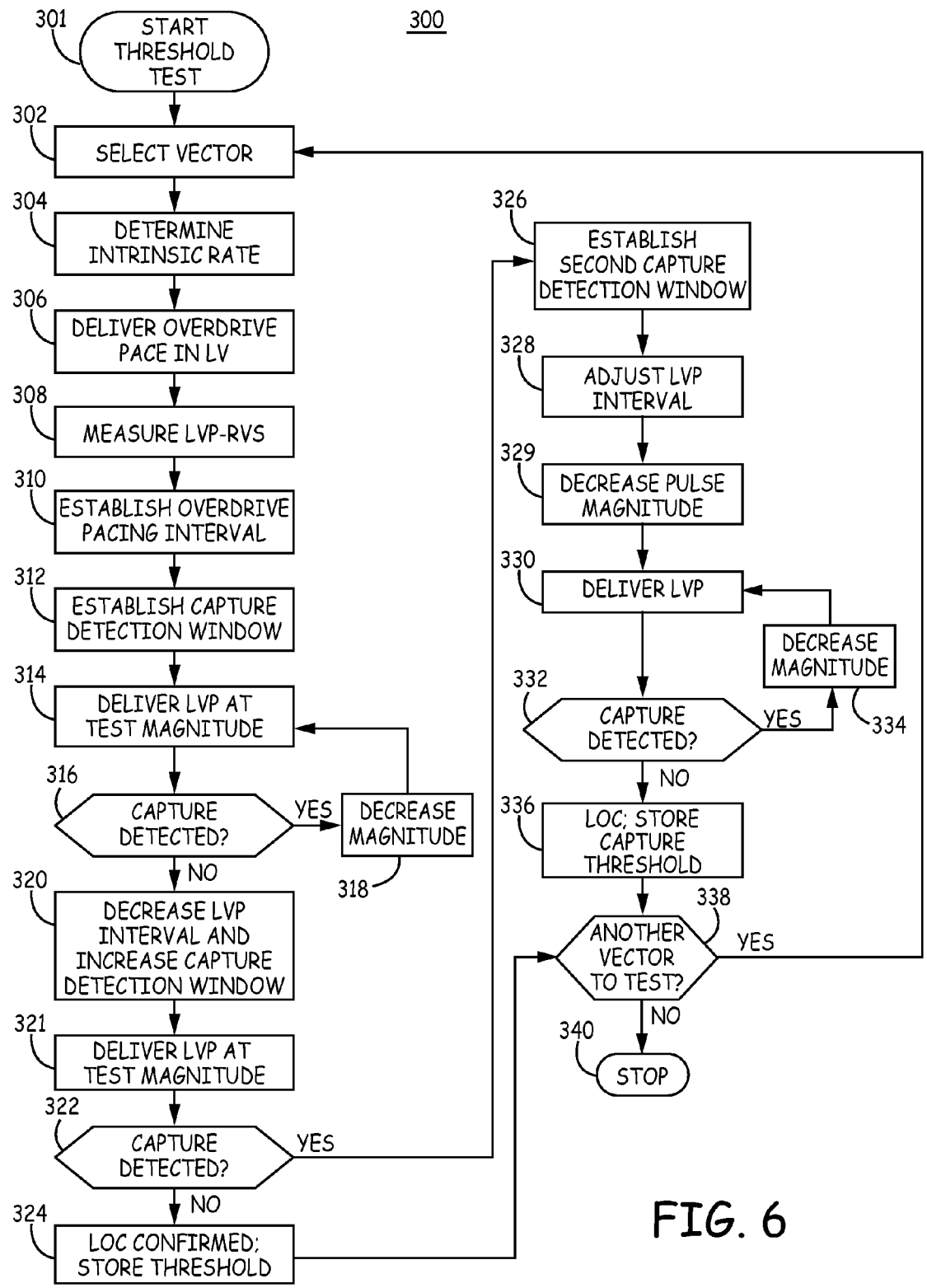
FIG. 6 is a flow chart of a method for performing a pacing capture threshold test according to an alternative embodiment.

FIG. 6 is a flow chart of a method 300 for performing a pacing capture threshold test according to an alternative embodiment. In FIG. 6, blocks 301 through 318 correspond to blocks 101 through 118 in FIG. 4. In FIG. 6, however, if capture is not detected based on an RVS sensed during the established capture detection window at block 316, the LVP interval is shortened and the capture detection window is increased at block 320 to give a wider "view" for detecting an RVS associated with an LVP evoked response.

Figure 7A:
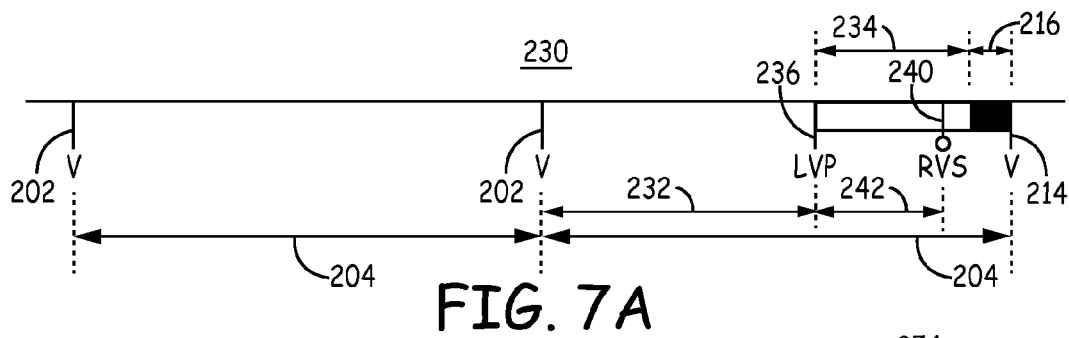
FIG. 7A is a timeline depicting a decreased overdrive pacing interval and increased capture detection window.

FIG. 7A is a time line 230 depicting a decreased overdrive pacing interval 232 (relative to the previously established LVP intervals 208') and increased capture detection window 234. In this example, the LVP interval 232 is decreased back to the original LVP interval 208 used to measure the LVP-RVS interval 212. The LVP interval 232 may be decreased to another interval but is generally decreased to be a shorter interval than the adjusted LVP interval 208' in FIG. 5B. This shorter LVP interval is followed by a capture detection window 234, which may extend from the LVP to the expected intrinsic RVS interval 216. By delivering the LVP 236 at a shorter interval 232, a longer capture detection window 234 can be used preceding the expected intrinsic RV sense interval 216.

As shown in FIG. 7A, an RVS event 240 may occur at a different LVP-RVS interval 242 than the LVP-RVS interval 212 previously measured as shown in FIG. 5B. A second, different LVP-RVS interval 242 can occur when anodal and cathodal capture occur for a given pacing vector. This second LVP-RVS interval 242 is evidence of a change in capturing electrode(s) during the capture test. For example at a higher voltage, both the anode and the cathode may capture while at a lower voltage only the cathode (or only the anode) may capture. By increasing the capture detection window 234, after decreasing the LVP interval 232, the second LVP-RVS interval 242 can be recognized and measured. Using this second LVP-RVS interval 242, a new LVP interval and new capture detection window can be established.

Figure 7B:
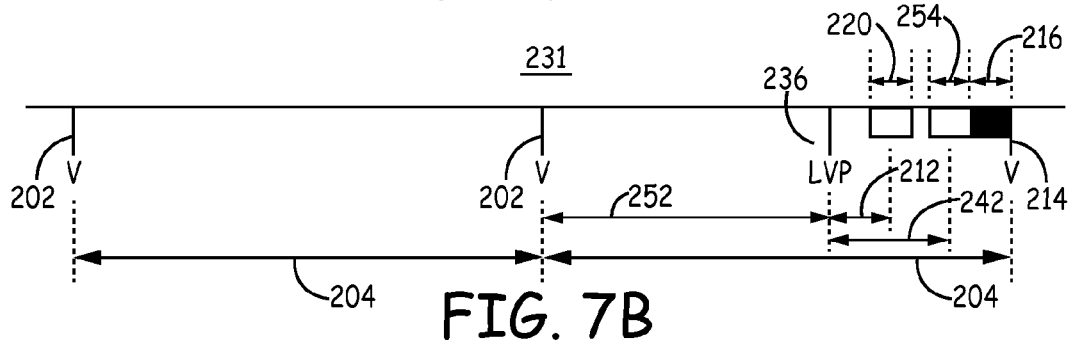
FIG. 7B is a timeline depicting an overdrive pacing interval that has been adjusted based on a second time interval measured between a pacing pulse in a first heart chamber and a sensed event in a second heart chamber after increasing the capture detection window as shown in FIG. 7A.

FIG. 7B is a timeline 231 depicting a LVP interval 252 that has been adjusted based on the second LVP-RVS interval 242 measured after decreasing the LVP interval 232 and increasing the capture detection window 234 as shown in FIG. 7A. The LVP interval 252 may be established as the intrinsic event rate interval 204 less the expected intrinsic event interval 216, less the second LVP-RVS interval 242, less half the predetermined duration of the capture detection window 254. This second adjusted LVP interval 252 is shorter than the first adjusted LVP interval 232 to allow a capture detection window 254 to be established prior to the expected intrinsic event interval 216 and approximately centered on the time of the RVS event 240 of the second LVP-RVS interval 242.

The first capture detection window 220 may be used to detect an RVS corresponding to the first LVP-RVS interval 212. Accordingly, after identifying and measuring a second LVP-RVS interval 242, two distinct first and second capture detection windows 220 and 254 may be separately defined, each corresponding to the respective first and second LVP-RVS intervals 212 and 242. The first and second capture detection windows 220 and 254 span different time intervals but may be overlapping time intervals in some cases. The LVP interval 252 is set to an interval that allows each capture detection window 220 and 254 to expire prior to the onset of the expected intrinsic event interval 216 without excessively overdrive pacing the ventricles. In this way, an RVS corresponding to capture at the anode or at the cathode in the LV can be reliably discriminated from an intrinsic event 214 that would occur if the LVP does not capture. An RVS occurring during either capture detection window 220 or 254 is evidence of capture by the LVP 256.

Referring again to FIG. 6, after decreasing the LVP interval at block 320 and lengthening the capture detection window, an LVP is delivered at block 321, which may be at the same pulse energy magnitude delivered last at block 314 when capture was not detected during the previously established capture detection window. If no RVS occurs in the extended capture detection window (see window 234 in FIG. 7A), capture is not detected at block 322. LOC is confirmed at block 324 and the lowest pulse magnitude that resulted in an RVS during the capture detection window is stored as the capture threshold for the current test vector. In some embodiments, an RVS during the expected intrinsic event window 216 is identified to confirm LOC.

However, if an RVS event is sensed during the lengthened capture detection window at block 322, a second capture detection window is established at block 326. The overdrive LVP interval is adjusted at block 328 as described above in conjunction with FIG. 7B. The LVP pulse magnitude may be decreased at block 329 from the magnitude that resulted in capture during the lengthened capture detection window at block 322. A LVP is delivered at the adjusted LVP interval at block 330. If an RVS event is sensed during either capture detection window 220 or 254 (FIG. 7B), capture is detected at block 332.

The pulse magnitude continues to be iteratively decreased at block 334 until capture is no longer detected, i.e. no RVS event occurs during either capture detection window. The lowest pulse magnitude that resulted in capture is stored as the capture threshold for the current test vector at block 336. If additional test vectors are available, as determined at block 338, the process returns to block 304 to select the next test vector. Otherwise, the capture threshold test is complete and the process is terminated at block 340.

Figure 7C:
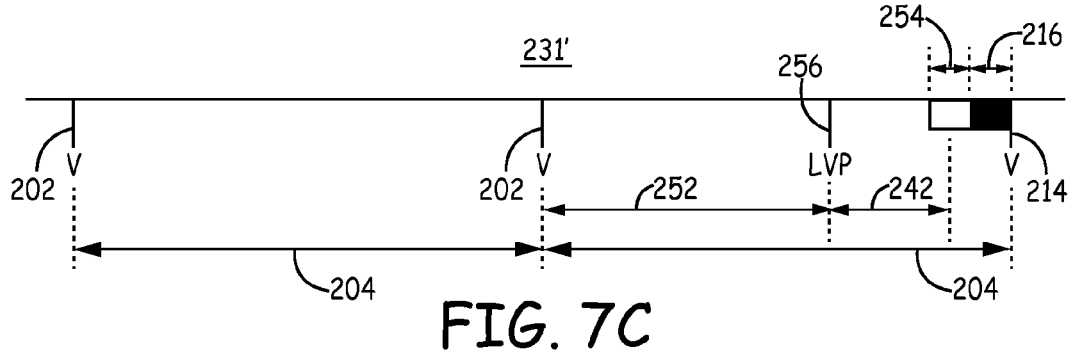
FIG. 7C is a timeline depicting an alternative method of applying a second capture detection window after capture is not detected during a first capture detection window.

In an alternative embodiment, the first capture detection window 220 may no longer be used when an RVS event is no longer sensed during the first capture detection window. As shown in the timeline 231' of FIG. 7C, after establishing the second capture detection window 254 in response to no RVS event during the first capture detection window 220, subsequent capture testing for the current LV pacing vector may involve identifying RVS events during the second capture window 254 only. Loss of capture has occurred at the electrode that resulted in the first LVP-RVS interval 212. The capture threshold test continues until loss of capture has also occurred at the electrode that resulted in the second LVP-RVS interval 242.

Figure 8:
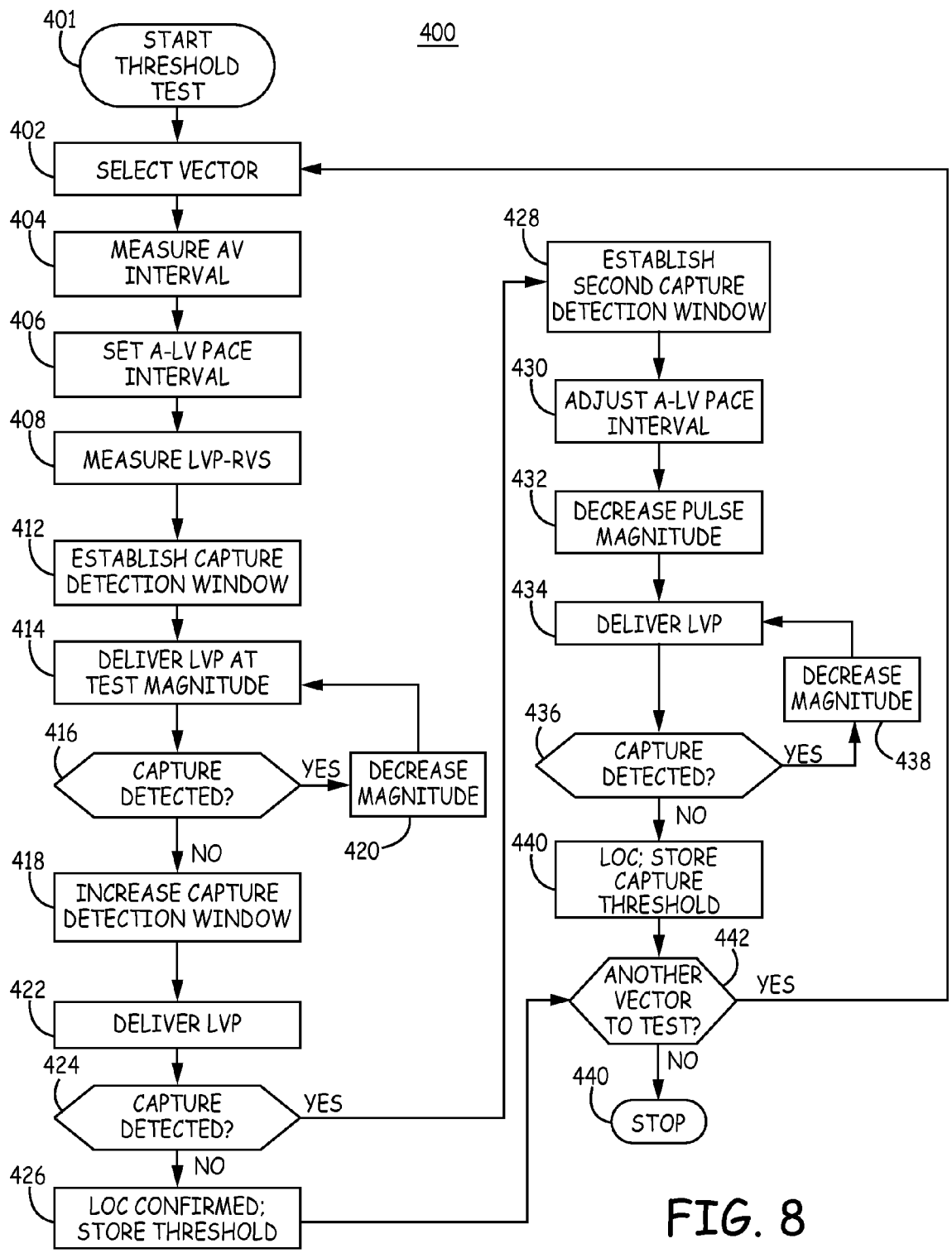
FIG. 8 is a flow chart of a method for determining a capture threshold according to an alternative embodiment.

FIG. 8 is a flow chart 400 of a method for determining a capture threshold according to an alternative embodiment. The method illustrated by flow chart 400 is similar to the method of FIG. 6, however, LV pacing is performed at a shortened A-LV interval rather than at a ventricular overdrive pacing rate. The techniques described above, which utilize ventricular overdrive pacing are useful in patients when dual chamber pacing is not available, for example in patients having AF or having a ventricular-only device for pacing and sensing in the ventricular chambers without sensing in the atrial chambers. The techniques described in conjunction with flow chart 400 may be implemented when atrial sensing and/or atrial pacing is available.

In FIG. 8, a capture threshold test is initiated at block 401. A pacing vector to be tested is selected at block 402, e.g. an LV pacing vector selected from a quadripolar lead as described above. At block 404, an intrinsic A-RV interval is measured to establish a time of an expected RVS event. An A-LV pace interval is set to be earlier than the expected RVS event at block 406 to promote capture of the LV and RV with a high probability prior to any intrinsic ventricular activity.

At block 408, an LVP is delivered and the LVP-RVS interval is measured. The LVP is delivered at the set A-LVP interval and at a pacing pulse energy magnitude that is highly likely to capture the LV. The measured LVP-RVS interval may be used to establish a capture detection window at block 412, during which an RVS indicates capture of a preceding LVP.

Figure 9A:
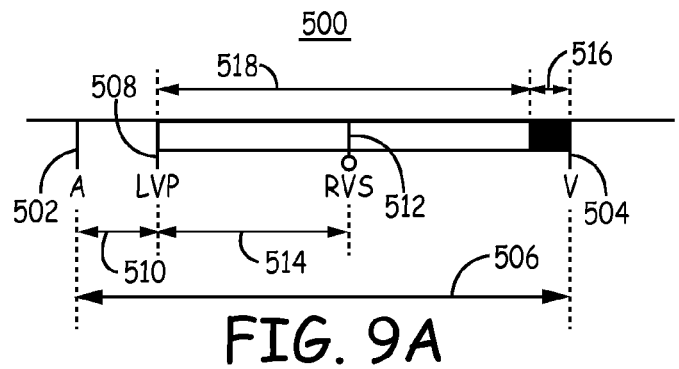
FIG. 9A is a timeline depicting dual chamber sensing and ventricular pacing for performing a ventricular capture threshold measurement.

FIG. 9A is a timeline 500 depicting dual chamber sensing and LV pacing for performing an LV capture threshold measurement. An A-RVS interval 506 is measured following an atrial event 502 (sensed or paced) until an intrinsic RVS event 504. An A-LVP interval 510 is then set as an interval shorter than the A-RVS interval 506 that allows the LVP evoked response to conduct to the RV causing an RVS event 512 to occur earlier than the expected intrinsic RVS 504. Initially, the A-LVP interval 510 may be set very short, for example at approximately 10 to 20 ms, to enable a relatively long sensing window 518 for identifying the RVS 512 as evidence of LV capture. Window 518 for sensing an RVS event 512 may extend for any or all of the interval between the LVP 508 and the onset of an expected intrinsic RVS interval 516. The LVP-RVS interval 514 is measured to establish a capture detection window as shown in FIG. 9B.

Figure 9B:
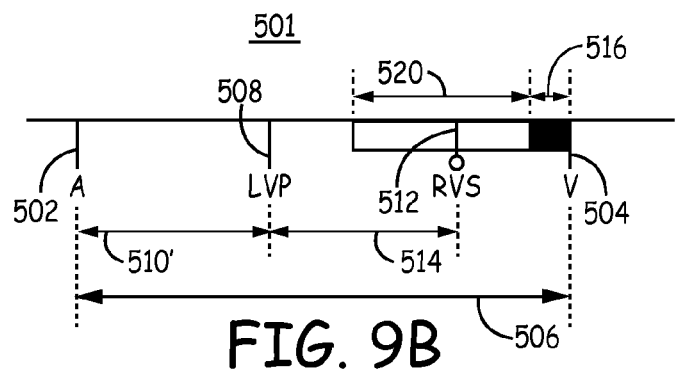
FIG. 9B is a timeline depicting a capture detection window established in response to a measured time interval between a pacing pulse delivered in a first heart chamber and a sensed event in a second heart chamber.

FIG. 9B is a timeline 501 depicting a capture detection window 520 established in response to a measured LVP-RVS interval 514. The capture detection window 520 may be set to a predetermined time duration, e.g. 30 ms, approximately centered at the time of the RVS event 512 and expiring at or prior to the onset of the expected intrinsic RVS time interval 516.

Optionally, the initial nominal A-LVP interval 510 may be adjusted to an A-LVP interval 510' that will be used during the capture test. The adjusted A-LVP interval may be set as the measured AV interval 506 less the expected intrinsic event interval 516, less the LVP-RVS interval 514 less half of the capture detection window 520. This adjusted A-LVP interval 510' may be longer than the nominal A-LVP interval used initially for measuring an LVP-RVS interval. The adjusted A-LVP interval 510' may be selected to allow for a more physiologic AV interval to preserve a more hemodynamically desirable timing relationship between the atria and ventricles while enabling the capture detection window 520 to expire prior to the onset of the expected intrinsic event interval 516. Alternatively, the nominal AV interval 510 may be used throughout the capture detection test.

As the LVP pulse magnitude is decreased or increased, an RVS 512 occurring any time during the capture detection window 520 is evidence that the LVP 508 captured the LV. If no RVS 512 is sensed during the capture detection window 520, the LVP may have lost capture.

Referring again to FIG. 8, after establishing a capture detection window at block 412, an LVP is delivered at block 414 at the nominal or an adjusted A-LVP interval at an initial test pulse energy magnitude (that has been established to cause capture as described above in conjunction with FIG. 4). If an RVS event is sensed during the capture detection window, capture is detected at block 416. The pulse energy magnitude is decreased at block 420 and this process repeats until no RVS event occurs during the capture detection window.

If capture is not detected, an adjustment is made at block 418 to lengthen the capture detection window. The capture detection window is lengthened to enable identification of a second LVP-RVS interval due to anodal capture. The capture detection window may be lengthened by extending the window to a longer interval, which may be up to the entire interval between the LVP and the onset of the expected intrinsic event interval. The A-LVP interval may also be shortened back to a nominal interval to enable lengthening of the capture detection window if an adjusted A-LVP interval 510' was used as described in conjunction with FIG. 9B.

Figure 10A:
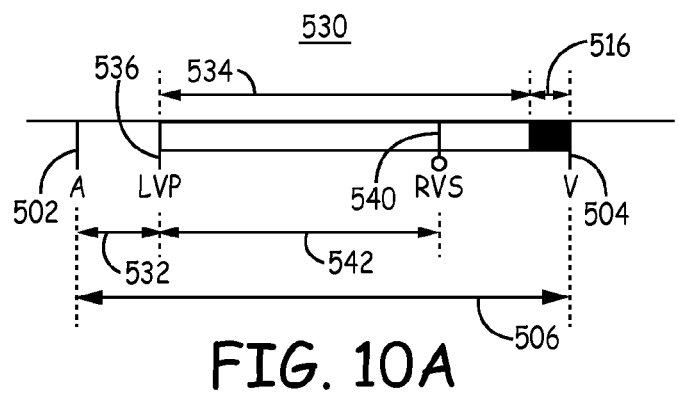
FIG. 10A is a timeline depicting an adjusted capture detection window established in response to not detecting capture during the previous capture detection window.

FIG. 10A is a timeline 530 depicting an adjusted capture detection window 534 established in response to not detecting capture during the previous capture detection window 520 (FIG. 9B). The capture detection window 534 is lengthened to extend from the LVP 536 to the onset of the expected intrinsic event interval 516. Lengthening of the capture detection window 534 may include decreasing the A-LVP interval 532, which may be shortened to be equal to the initial nominal A-LVP interval 510 shown in FIG. 9A. The lengthened capture detection window 534 is shown to extend from LVP 536 to the onset of the expected intrinsic sensed event interval 518.

An RVS event 540 may occur at a second LVP-RVS interval 542 that is different than the first LVP-RVS interval 512. This second LVP-RVS interval 542 is evidence that anodal and cathodal capture are occurring during the capture test. Accordingly, a second capture detection window corresponding to the second LVP-RVS interval 542 may be established.

Figure 10B:
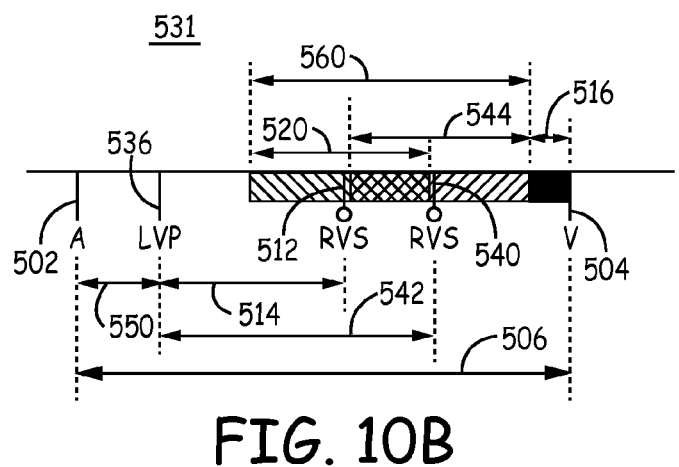
FIG. 10B is a timeline depicting first and second capture detection windows.

FIG. 10B is a timeline 531 depicting first and second capture detection windows 520 and 544 each approximately centered on the time of an RVS 512 and 540 of respective LVP-RVS intervals 514 and 542. Each of the first and second capture detection windows 520 and 544 expire prior to the expected intrinsic event interval 516 such that an RVS associated with capture of the LV by LVP 536 can be discriminated from an intrinsic RVS 504.

The A-LVP interval 550 may be adjusted to a maximum interval that allows both of the first and second capture detection windows to expire prior to the expected intrinsic event interval 504. Alternatively, as shown in FIG. 10B, the A-LVP interval 550 may be kept equal to the short, nominal interval 510 shown in FIG. 9A. As described previously, if capture is lost during the first capture detection window 520, only the second capture detection window 544 may be applied during subsequent capture tests at decreasing pulse energy magnitudes.

It is further noted that the first and second capture detection windows 520 and 544 may overlap. In some embodiments, a single new capture detection window 560 may be established that encompasses both the end time of the first LVP-RVS interval 512 and the end time of the second LVP-RVS interval 540. In other words, a single new capture detection window 560 may extend from the beginning of the first capture detection window 520 to the end of the second capture detection window 544. This new capture detection window 560 expires before the expected intrinsic event 504 but would exclude premature ventricular contractions that might occur after LVP 536, outside window 560 as being evidence of LV capture.

With continued reference to FIG. 8, after lengthening the capture detection window at block 418, an LVP is delivered at block 422 at the last pulse energy at which capture was not detected during the previous capture detection window. If capture is still not detected at block 424 during the lengthened capture detection window, LOC is confirmed at block 426. The lowest pulse energy magnitude that resulted in capture detection is stored as the capture threshold for the test pacing vector.

If an RVS event is sensed during the lengthened capture detection window at block 424, a second capture detection window is established at block 428 as described in conjunction with FIG. 10B. If an A-LVP interval used during the capture test had been lengthened from a nominal, short A-LVP interval (as shown in FIG. 9B), it may be shortened back to the nominal A-LVP interval to accommodate the second capture detection window at block 430. Alternatively, a short A-LVP interval is used throughout the capture detection test.

At block 432 the pulse energy magnitude is decreased from the last test pulse that resulted in a capture detection, and the LVP is delivered at the decreased pulse energy at block 434. If capture is detected at block 436 based on an RVS event during the second capture detection window, the pulse energy magnitude continues to be decreased at block 438 until capture is no longer detected.

When no RVS event occurs during either capture detection window, LOC is confirmed. The capture threshold is stored at block 440 as the lowest pacing pulse energy that resulted in capture detection. If any other pacing vectors remain to be tested after storing a capture threshold for the current test vector, as determined at block 442, the process returns to block 404 to select the next test vector. Otherwise, the capture threshold test is completed at block 440.

Various embodiments of a capture threshold test have been described. These and other examples are within the scope of the following claims.

The invention claimed is:

1. A method for facilitating selection of a vector from among a plurality of pacing vectors for pacing a first chamber of a heart, the method comprising:
    delivering a pacing pulse to capture a first heart chamber using a combination of electrodes comprising at least a first electrode and a second electrode of the plurality of pacing vectors;
    determining a first time interval between the pacing pulse and a sensed event in a second heart chamber;
    determining a capture detection window in response to the determined first time interval;
    iteratively decreasing a pacing pulse magnitude delivered in the first heart chamber until an event in the second heart chamber is not sensed during the determined capture detection window;
    lengthening the capture detection window in response to a depolarization of the second heart chamber not being sensed during the determined capture detection window; and
    detecting a change in capturing electrodes of the combination of electrodes in response to sensing an event in the second heart chamber during the lengthened capture detection window after not sensing an event in the second heart chamber during the determined capture detection window.

2. The method of claim 1, further comprising lengthening the capture detection window by starting the lengthened capture detection window earlier than the determined capture detection window.

3. The method of claim 2, further comprising:
    responsive to sensing the event in the second heart chamber during the lengthened capture detection window, determining a second time interval between a pacing pulse delivered to the first heart chamber and the sensed event in the second heart chamber;
    determining a second capture detection window in response to the second determined time interval, the second capture detection window spanning a different time interval than the first capture detection interval; and
    iteratively decreasing a pacing pulse magnitude until an event in the second heart chamber is not sensed during the second capture detection window.

4. The method of claim 1, further comprising:
    determining a cardiac interval between a first event other than the pacing pulse delivered to capture the first heart chamber and an intrinsic event sensed in the second heart chamber;
    determining an expected intrinsic event time interval in response to the sensed intrinsic event; and
    determining a pacing interval for delivering pacing pulses in the first heart chamber in response to the determined first time interval between the pacing pulse and a sensed event in a second heart chamber and the expected intrinsic event time interval.

5. The method of claim 4, further comprising lengthening the capture detection window in response to a depolarization of the second heart chamber not being sensed during the determined capture detection window.

6. The method of claim 5, wherein lengthening the capture detection window comprises decreasing the determined pacing interval to a second pacing interval shorter than the first pacing interval.

7. The method of claim 1, wherein iteratively decreasing the pacing pulse magnitude comprises delivering pacing pulses in the first heart chamber at a ventricular overdrive pacing interval.

8. The method of claim 7 further comprising determining a maximum ventricular overdrive pacing interval that allows the capture detection window to expire prior to an expected intrinsic event in the second heart chamber.

9. The method of claim 1, wherein iteratively decreasing the pacing pulse magnitude comprises delivering pacing pulses in the first heart chamber at an atrial-ventricular pacing interval.

10. The method of claim 1, further comprising:
lengthening the capture detection window in response to a depolarization of the second heart chamber not being sensed during the determined capture detection window;
determining a second capture detection window in response to sensing a depolarization of the second heart chamber during the lengthened capture detection window; and
recording a capture threshold for each of the plurality of pacing vectors corresponding to a minimum pacing pulse magnitude resulting in a depolarization of the second heart chamber being sensed in one of the first capture detection window and the second capture detection window.

11. The method of claim 1, wherein the detected change in capturing electrodes is detected as the pacing pulse magnitude is iteratively decreased and comprises a loss of capture at one of the first electrode and the second electrode and capture at the other of the first electrode and the second electrode.

12. A medical device for facilitating selection of a pacing vector from among a plurality of pacing vectors for pacing a first chamber of a heart, the device comprising:
a plurality of electrodes;
a signal generator coupled to the plurality of electrodes for delivering pacing pulses to a patient's heart;
a sensing module coupled to the plurality of electrodes for sensing cardiac event signals; and
a capture detection module coupled to the signal generator and the sensing module and configured to:
control the signal generator to deliver a pacing pulse to capture a first heart chamber using a combination of electrodes comprising at least a first electrode and a second electrode of the plurality of pacing vectors;
determine a first time interval between the pacing pulse and a sensed event in a second heart chamber;
determine a capture detection window in response to the determined first time interval;
iteratively decrease a pacing pulse magnitude delivered in the first heart chamber until an event in the second heart chamber is not sensed during the determined capture detection window;
lengthening the capture detection window in response to a depolarization of the second heart chamber not being sensed during the determined capture detection window; and
detecting a change in capturing electrodes of the combination of electrodes in response to sensing an event in the second heart chamber during the lengthened capture detection window after not sensing an event in the second heart chamber during the determined capture detection window.

13. The device of claim 12, wherein the capture detection module is further configured to lengthen the capture detection window by starting the lengthened capture detection window earlier than the determined capture detection window.

14. The device of claim 13, wherein the capture detection module is further configured to:
responsive to sensing the event in the second heart chamber during the lengthened capture detection window, determine a second time interval between a pacing pulse delivered to the first heart chamber and the sensed event in the second heart chamber;
determine a second capture detection window in response to the second determined time interval, the second capture detection window spanning a different time interval than the first capture detection interval; and
iteratively decrease a pacing pulse magnitude until an event in the second heart chamber is not sensed during the second capture detection window.

15. The device of claim 12, wherein the capture detection module is further configured to:
determine a cardiac interval between a first event other than the pacing pulse delivered to capture the first heart chamber and an intrinsic event sensed in the second heart chamber;
determine an expected intrinsic event time interval in response to the sensed intrinsic event; and
determine a pacing interval for delivering pacing pulses in the first heart chamber in response to the determined first time interval between the pacing pulse and a sensed event in a second heart chamber and the expected intrinsic event time interval.

16. The device of claim 15, wherein the capture detection module is further configured to lengthen the capture detection window in response to a depolarization of the second heart chamber not being sensed during the determined capture detection window.

17. The device of claim 16 wherein lengthening the capture detection window comprises decreasing the determined pacing interval to a second pacing interval shorter than the first pacing interval.

18. The device of claim 12, wherein the capture detection module is further configured to iteratively decrease the pacing pulse magnitude in the first heart chamber at a ventricular overdrive pacing interval.

19. The device of claim 18, wherein the capture detection module is further configured to determine a maximum ventricular overdrive pacing interval that allows the capture detection window to expire prior to an expected intrinsic event in the second heart chamber.

20. The device of claim 12, wherein the capture detection module is further configured to iteratively decrease the pacing pulse magnitude in the first heart chamber at an atrial-ventricular pacing interval.

21. The device of claim 12, wherein the capture detection module is further configured to:
lengthen the capture detection window in response to a depolarization of the second heart chamber not being sensed during the determined capture detection window;
determine a second capture detection window in response to sensing a depolarization of the second heart chamber during the lengthened capture detection window; and
record a capture threshold for each of the plurality of pacing vectors corresponding to a minimum pacing pulse magnitude resulting in a depolarization of the second heart chamber being sensed in one of the first capture detection window and the second capture detection window.

22. A non-transitory, computer-readable storage medium comprising instructions that, when executed by a processor, cause the processor to:
- control a signal generator to deliver a pacing pulse to capture a first heart chamber using a combination of electrodes comprising at least a first electrode and a second electrode of a plurality of pacing vectors;
- determine a first time interval between the pacing pulse and a sensed event in a second heart chamber;
- determine a capture detection window in response to the determined first time interval; and
- enable a capture detection module to iteratively decrease a pacing pulse magnitude delivered in the first heart chamber until an event in the second heart chamber is not sensed during the determined capture detection window;
- lengthen the capture detection window in response to a depolarization of the second heart chamber not being sensed during the determined capture detection window; and
- detect a change in capturing electrodes of the combination of electrodes in response to sensing an event in the second heart chamber during the lengthened capture detection window after not sensing an event in the second heart chamber during the capture detection window.

* * * * *